United States Patent
Kambayashi et al.

(10) Patent No.: US 8,540,169 B2
(45) Date of Patent: Sep. 24, 2013

(54) ATOMIZING MEMBER AND ATOMIZER INCLUDING THE SAME

(75) Inventors: Tsuguji Kambayashi, Nagaokakyo (JP);
Katsumi Fujimoto, Nagaokakyo (JP);
Hiroaki Kaida, Nagaokakyo (JP);
Daisuke Nakamura, Nagaokakyo (JP)

(73) Assignee: Murata Manufacturing Co., Ltd., Nagaokakyo-Shi, Kyoto-fu (JP)

(*) Notice: Subject to any disclaimer, the term of this patent is extended or adjusted under 35 U.S.C. 154(b) by 114 days.

(21) Appl. No.: 13/190,561

(22) Filed: Jul. 26, 2011

(65) Prior Publication Data

US 2011/0284656 A1 Nov. 24, 2011

Related U.S. Application Data

(63) Continuation of application No. PCT/JP2009/005978, filed on Nov. 10, 2009, and a continuation of application No. PCT/JP2010/051386, filed on Feb. 2, 2010.

(30) Foreign Application Priority Data

Feb. 9, 2009 (JP) ................................. 2009-027229

(51) Int. Cl.
*B05B 1/08* (2006.01)

(52) U.S. Cl.
USPC .................................... 239/102.2; 239/102.1

(58) Field of Classification Search
USPC ................... 239/102.2, 102.1, 589.1
See application file for complete search history.

(56) References Cited

U.S. PATENT DOCUMENTS

| | | | | |
|---|---|---|---|---|
| 3,806,029 | A | * | 4/1974 | Hughes ............................ 239/3 |
| 4,530,464 | A | * | 7/1985 | Yamamoto et al. ......... 239/102.2 |
| 4,533,082 | A | | 8/1985 | Maehara et al. |
| 5,217,171 | A | * | 6/1993 | Feldman ......................... 241/20 |
| 6,497,019 | B1 | * | 12/2002 | Yun ............................. 29/25.35 |
| 7,140,554 | B2 | * | 11/2006 | Chang ........................ 239/102.2 |

FOREIGN PATENT DOCUMENTS

| | | |
|---|---|---|
| JP | 58-067374 A | 4/1983 |
| JP | 60-068071 A | 4/1985 |
| JP | 62-046226 | 10/1987 |
| JP | 1-038244 A | 2/1989 |
| JP | 64-38244 A | 2/1989 |
| JP | 6-007721 A | 1/1994 |
| JP | 63-11063 A | 11/1994 |

OTHER PUBLICATIONS

PCT/JP2009/005978 International Seach Report Aug. 2, 2010.
PCT/JP2009/005978 Written Opinion dated Aug. 2, 2010.

* cited by examiner

*Primary Examiner* — Davis Hwu
(74) *Attorney, Agent, or Firm* — Dickstein Shapiro LLP

(57) ABSTRACT

An atomizing member that includes a piezoelectric vibrator and a vibrating membrane. The piezoelectric vibrator includes a cylindrical piezoelectric body, a first electrode disposed on an inner circumferential surface of the piezoelectric body, and a second electrode disposed on an outer circumferential surface of the piezoelectric body. The piezoelectric vibrator performs cylindrical breathing vibration. The vibrating membrane is disposed on an opening at a first side in an axial direction of the piezoelectric body so as to cover the opening. The vibrating membrane has a through hole in its central portion.

17 Claims, 13 Drawing Sheets

ATOMIZING MEMBER AND ATOMIZER INCLUDING THE SAME

CROSS REFERENCE TO RELATED APPLICATIONS

The present application is a continuation of International Application No. PCT/JP2009/005978, filed Nov. 10, 2009, and International Application No. PCT/JP2010/051386, filed Feb. 2, 2010, which each claim priority to Japanese Patent Application No. JP2009-027229, filed Feb. 9, 2009, the entire contents of each of these applications being incorporated herein by reference in their entirety.

FIELD OF THE INVENTION

The present invention relates to atomizing members and, specifically, to an ultrasonic atomizing member that uses a piezoelectric vibrator and an atomizer including the same.

BACKGROUND OF THE INVENTION

Previously, various atomizers each using a piezoelectric vibrator have been proposed, for example, as described in Patent Literature 1 below. FIG. 9 illustrates a cross-section view of an atomizer described in Patent Literature 1.

As illustrated in FIG. 9, an atomizer 100 includes a base 101 in which a pressurized room 102 for allowing being filled with liquid to be atomized is disposed. A nozzle plate 103 is fixed to the base 101 so as to cover an upper opening 102a of the pressurized room 102. The nozzle plate 103 has many nozzle orifices at its central portion. A disc-shaped piezoelectric vibrator 104 having an opening 104a formed at its central portion is attached on the nozzle plate 103.

The piezoelectric vibrator 104 includes a disc-shaped piezoelectric body 105 and first and second electrodes 106 and 107. The first and second electrodes 106 and 107 are disposed on an upper surface 105a and a lower surface 105b of the piezoelectric body 105, respectively. The piezoelectric vibrator 104 is configured so as to be vibrated by transverse effects. That is, the piezoelectric vibrator 104 vibrates in a diametrical direction.

For the atomizer 100, as illustrated in FIGS. 10 and 11, vibration of the piezoelectric vibrator 104 by transverse effects causes flexural vibration of the nozzle plate 103 in a direction z perpendicular to the planar direction of the piezoelectric vibrator 104. As a result, liquid in the pressurized room 102 is sprayed through the nozzle orifices of the nozzle plate 103.

Patent Literature 1: Japanese Examined Patent Application Publication No. 63-11063

SUMMARY OF THE INVENTION

Patent Literature 1 above describes that the use of the piezoelectric vibrator 104 vibrated by transverse effects can provide the atomizer 100 having a simple structure, being compact, achieving good atomization performance, and consuming less power.

However, as described in Patent Literature 1, when the piezoelectric vibrator vibrated by transverse effects is used, it is difficult to sufficiently increase atomization efficiency, and accordingly, there is a problem in that it is difficult to sufficiently reduce the power consumption.

It is an object of the present invention to provide an atomizing member that uses a piezoelectric vibrator and an atomizer that includes the atomizing member, the atomizing member being capable of having high atomization efficiency and low power consumption.

An atomizing member according to the present invention includes a piezoelectric vibrator and a vibrating membrane. The piezoelectric vibrator includes a cylindrical piezoelectric body, a first electrode, and a second electrode. The first electrode is disposed on an inner circumferential surface of the piezoelectric body. The second electrode is disposed on an outer circumferential surface of the piezoelectric body. The piezoelectric vibrator performs cylindrical breathing vibration. The vibrating membrane is disposed on an opening at a first side in an axial direction of the piezoelectric body so as to cover the opening. The vibrating membrane has a through hole in a central portion thereof.

In a particular aspect of the atomizing member according to the present invention, the piezoelectric body and the vibrating membrane are formed integrally with each other. With this configuration, not only the piezoelectric vibrator can be produced easily, but also vibration efficiency of the piezoelectric vibrator can be enhanced.

In another particular aspect of the atomizing member according to the present invention, the piezoelectric vibrator includes a flange connected to a section at the first side in the axial direction of the piezoelectric body, the flange is outwardly extending in its diametrical direction from the section at the first side. For this configuration, because the atomizing member can be mounted at the flange, the atomizing member can be easily mounted. Because the flange is connected to the section at the first side in the axial direction of the piezoelectric body, the section having small displacement of vibration, even when the atomizing member is mounted at the flange, inhibition on the vibration of the piezoelectric body is small. Accordingly, a decrease in vibration efficiency in response to the mounting of the atomizing member on another member can be suppressed.

In yet another particular aspect of the atomizing member according to the present invention, the flange is formed integrally with the piezoelectric body. With this configuration, not only the piezoelectric vibrator including the flange can be formed easily, but also vibration efficiency of the piezoelectric vibrator can be enhanced.

In still another particular aspect of the atomizing member according to the present invention, a connection portion of the flange that is connected to the piezoelectric body has vibration propagation characteristics different from those of other sections of the flange. For this configuration, vibration of the piezoelectric body is reflected at the connection portion of the flange being connected to the piezoelectric body. Consequently, the vibration of the piezoelectric body is not conveyed to a section outside the connection portion of the flange. Accordingly, a decrease in vibration efficiency caused by the flange and a decrease in vibration efficiency caused by fixation of the flange to another member can be suppressed. In addition, the degree of freedom in design of the flange can be increased.

In yet a further particular aspect of the atomizing member according to the present invention, a connection portion of the flange that is connected to the piezoelectric body has a groove. For this configuration, vibration of the piezoelectric body is separated at the connection portion in which the groove is disposed. Consequently, the vibration of the piezoelectric body is not conveyed to a section outside the connection portion of the flange. Accordingly, a decrease in vibration efficiency caused by the flange and a decrease in vibration efficiency caused by fixation of the flange to another member can be suppressed. In addition, the degree of freedom in design of the flange can be increased.

In another particular aspect of the atomizing member according to the present invention, the piezoelectric vibrator further includes a first electrode pad connected to the first electrode and a second electrode pad connected to the second electrode, and the first and second electrode pads are disposed on a surface of the flange at a second side in the axial direction of the piezoelectric body. With this configuration, for example, when liquid to be atomized is supplied from the piezoelectric body side to the vibrating membrane, vapor is not easily attached to the first and second electrode pads. Accordingly, degradation of the first and second electrode pads resulting from cavitation erosion can be reduced.

In yet another particular aspect of the atomizing member according to the present invention, the central portion where the through hole of the vibrating membrane is disposed comprises a through-hole formed member being an element different from other sections of the vibrating membrane. With this configuration, because the through-hole formed member can be produced independently of other sections of the vibrating membrane, the vibrating membrane can be easily produced. In addition, the through-hole formed member can be made of a material different from that of the other sections of the vibrating membrane. Accordingly, the degree of freedom in design of the through-hole formed member and the other sections of the vibrating membrane can be improved, and the through-hole formed member and the other sections of the vibrating membrane can easily conform to specifications required for each member more precisely.

In still another particular aspect of the atomizing member according to the present invention, the through-hole formed member is made of metal. For this configuration, for example, in comparison with when the member forming the central portion where the through hole is disposed is made of ceramic, the through hole can be formed more easily. Accordingly, the vibrating membrane can be easily produced.

As the forming material of the through-hole formed member, resin that is easier to be processed can also be used.

In yet a further particular aspect of the atomizing member according to the present invention, the through-hole formed member is made of the same material as that of the sections of the vibrating membrane other than the through-hole formed member.

An atomizer according to the present invention includes the atomizing member according to the present invention described above, an atomizer main body, and a liquid feeder. The piezoelectric vibrator is mounted on the atomizer main body. The atomizer main body includes a storage for storing liquid. The liquid feeder supplies the liquid stored in the storage to the section of the vibrating membrane where the through hole is disposed.

In a particular aspect of the atomizer according to the present invention, the liquid feeder supplies the liquid from the second side in the axial direction of the piezoelectric body to the vibrating membrane. With this configuration, the angle of diffusion occurring in the vibrating membrane can be increased.

In another particular aspect of the atomizer according to the present invention, the piezoelectric vibrator includes a flange connected to a section at the first side in the axial direction of the piezoelectric body, the flange is outwardly extending in its diametrical direction from the section at the first side is including a peripheral portion in the diametrical direction supported by the atomizer main body. The flange includes at least two bridges formed by a plurality of through holes extending in its circumferential direction, the at least two bridges is connecting the peripheral portion and the vibrating membrane. A length of each of the at least two bridges is within a range of 30% to 50%, 70% to 90%, or 115% to 120% of a radius of the vibrating membrane. For this configuration, the occurrence of resonance of a frequency near the resonant frequency of the vibrating membrane can be efficiently reduced. Accordingly, the occurrence of unnecessary vibration can be reduced, and satisfactory atomization characteristics can be achieved.

In yet another particular aspect of the atomizer according to the present invention, a cut portion reaching a central portion in a thickness direction of the piezoelectric body is disposed at each of both sides of a section of the vibrating membrane in the circumferential direction, the section being connected to each of the bridges. A section positioned between the cut portions in the circumferential direction of the bridge is not connected to the piezoelectric body. Here, the central portion in the thickness direction of the piezoelectric body is a node. Therefore, with this configuration, the vibrating membrane can be supported at the node. Accordingly, more satisfactory atomization characteristics are obtainable.

In still another particular aspect of the atomizer according to the present invention, the piezoelectric body is arranged below the vibrating membrane in a vertical direction. For this configuration, the vibrating membrane is positioned below the peripheral portion by the weight of the piezoelectric body. Therefore, the bridge and the piezoelectric body are spaced away from each other. Consequently, contact between the bridge and the piezoelectric body can be reduced. Accordingly, abrasion of the bridge can be suppressed. As a result, the life of the atomizer can be increased.

With the present invention, because the vibrating membrane is driven by cylindrical breathing vibration of the cylindrical piezoelectric body, vibration efficiency of the vibrating membrane can be enhanced. Consequently, atomization efficiency can be high, and power consumption can be low.

BRIEF DESCRIPTION OF THE DRAWINGS

FIG. 10 is a cross-sectional view of the piezoelectric vibrator and the nozzle plate when the piezoelectric vibrator transversely extends.

FIG. 11 is a cross-sectional view of the piezoelectric vibrator and the nozzle plate when the piezoelectric vibrator transversely contracts.

DESCRIPTION OF THE INVENTION

The present invention is clarified below by description of an example of concrete embodiments of the present invention with reference to drawings.

First Embodiment

Figure 1:
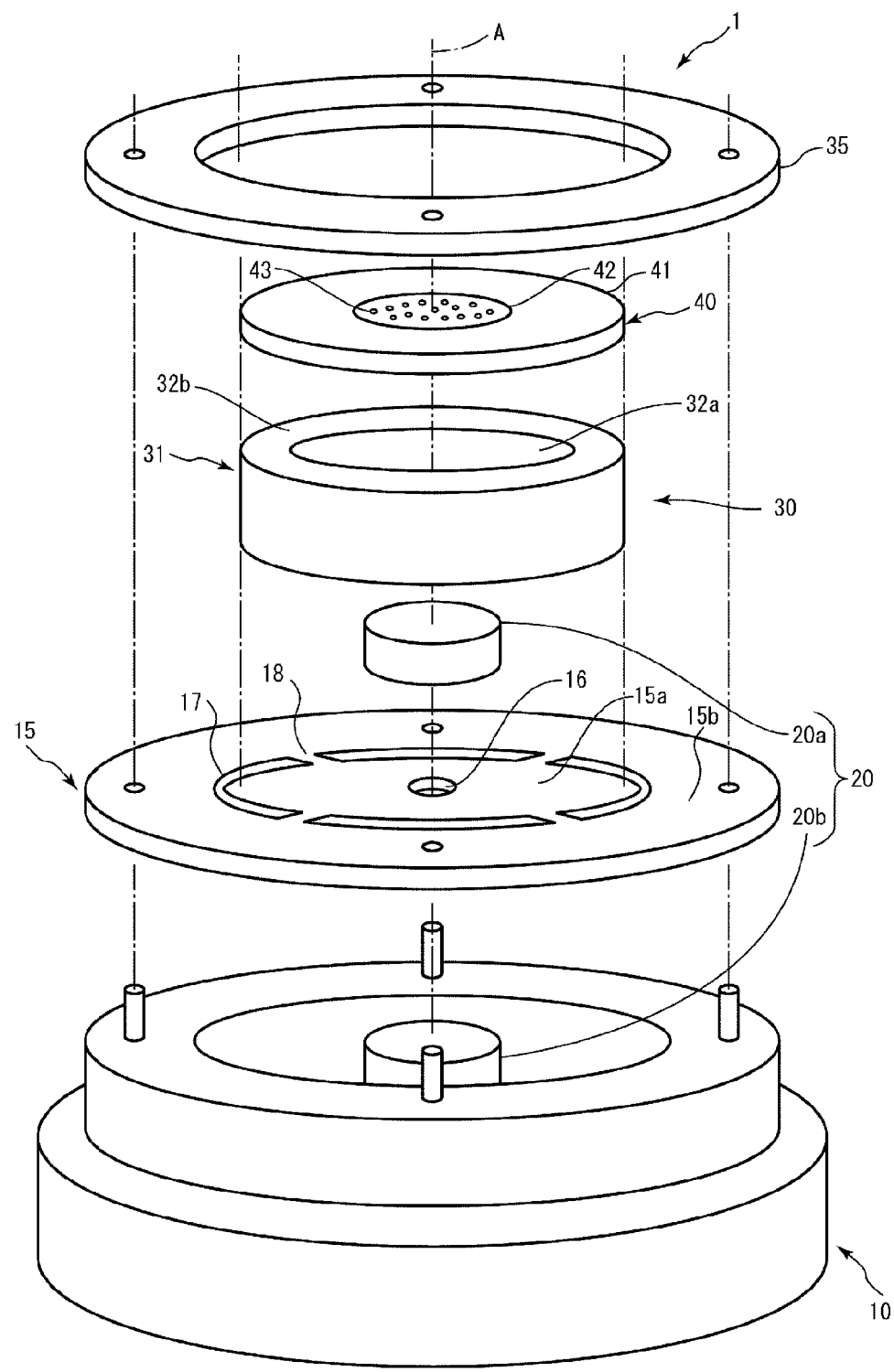
FIG. 1 is a schematic exploded perspective view of an atomizer of a first embodiment.
Figure 2:
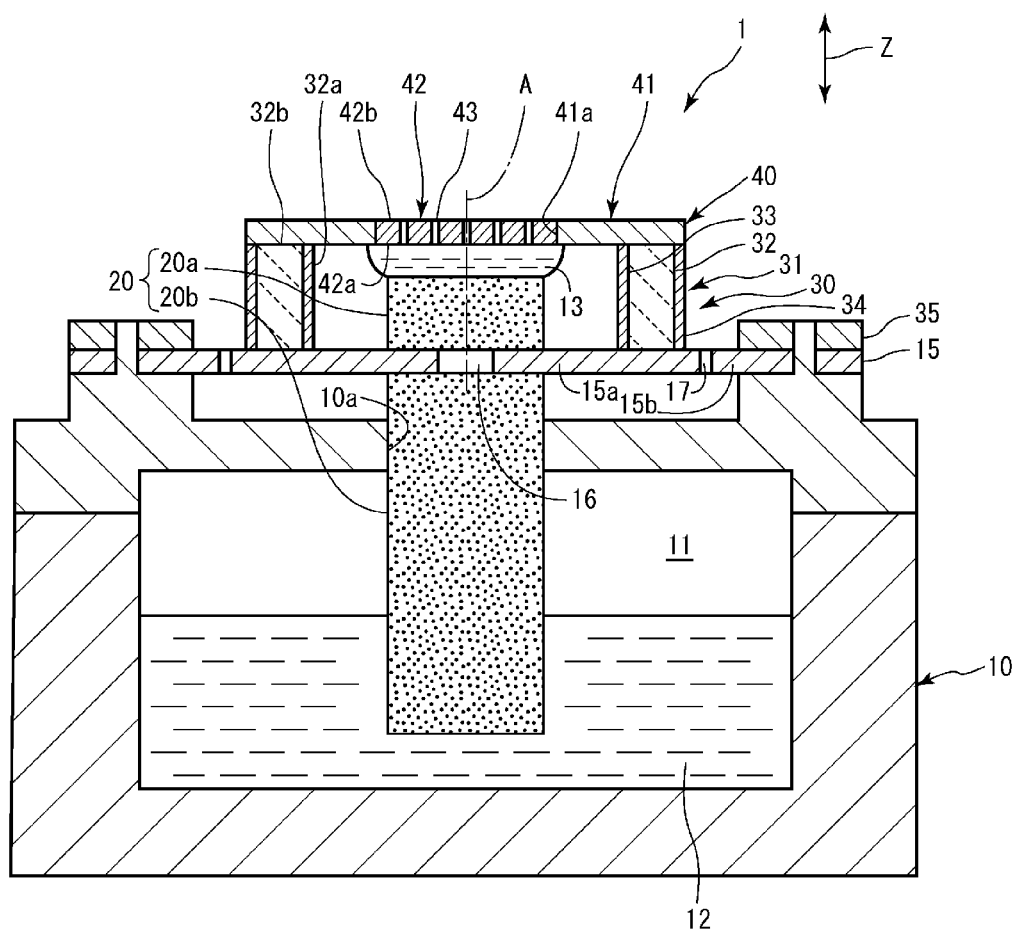
FIG. 2 is a schematic cross-sectional view of the atomizer of the first embodiment.

FIG. 1 is a schematic exploded perspective view of an atomizer of the first embodiment. FIG. 2 is a schematic cross-sectional view of the atomizer of the first embodiment. As illustrated in FIGS. 1 and 2, an atomizer 1 includes an atomizing member 30, an atomizer main body 10, and a liquid feeder 20. The atomizer 1 may further include a circuit for driving the atomizing member 30, for example. The circuit for driving the atomizing member 30 can have an oscillator circuit, a control circuit for the oscillator circuit, a power circuit for supplying power to each circuit, and other circuits, for example.

The atomizer main body 10 can be made of synthetic resin, metal, glass, ceramic, paper, and other materials, for example. As illustrated in FIG. 2, the atomizer main body 10 includes a storage 11 disposed therein. The storage 11 stores liquid 12 to be atomized. The liquid 12 is not particularly limited. Examples of the liquid 12 can include water, aqueous solution, and an organic solvent, such as alcohol and petroleum. The liquid 12 may be an aromatic substance, a deodorant, an insecticide, an insect repellent, perfumery, lotion, and detergent.

The atomizing member 30 is mounted on the atomizer main body 10 such that an elastic film 15 is disposed therebetween. Alternatively, the atomizing member 30 may be directly mounted on the atomizer main body 10.

As illustrated in FIGS. 1 and 2, the atomizing member 30 includes a cylindrical piezoelectric vibrator 31 and a vibrating membrane 40. As illustrated in FIG. 2, the piezoelectric vibrator 31 includes a cylindrical piezoelectric body 32. The piezoelectric body 32 is made of a piezoelectric material. The piezoelectric material for forming the piezoelectric body 32 is not particularly limited. Examples of the piezoelectric material can include lead zirconate titanate (PZT) ceramic. The dimensions of the piezoelectric body 32 are not particularly limited. The dimensions of the piezoelectric body 32 can be 10 mm in inside diameter, 12 mm in outside diameter, and 3.5 mm in height.

Figure 5A:
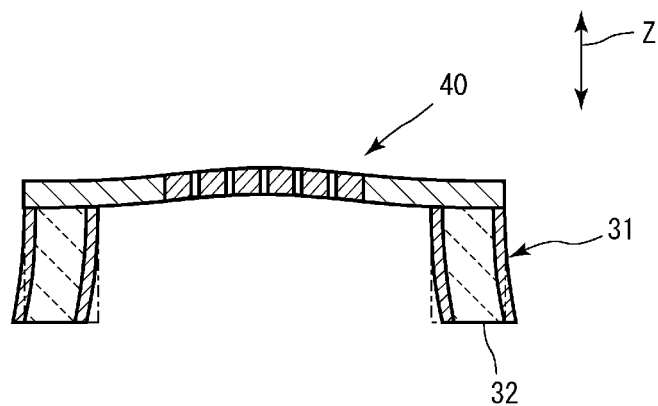
FIGS. 5(a) to 5(c) are diagrams describing mode of cylindrical breathing vibration of the piezoelectric vibrator.
Figure 5B:
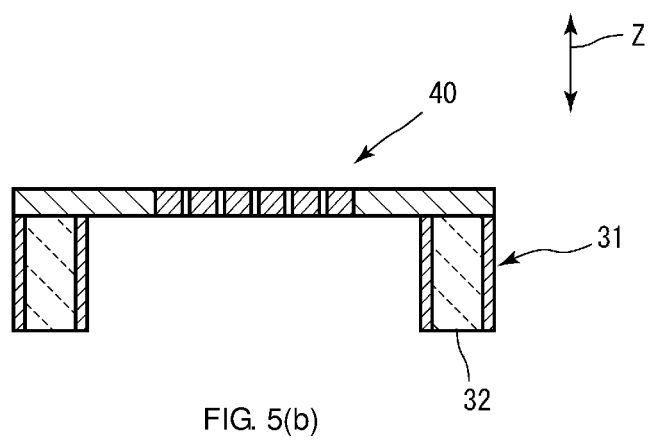
Figure 5C:
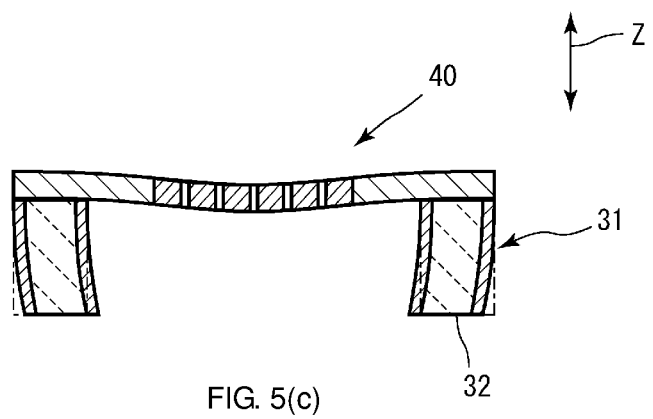

A first electrode 33 is disposed on the inner circumferential surface of the piezoelectric body 32. A second electrode 34 is disposed on the outer circumferential surface of the piezoelectric body 32. The piezoelectric body 32 is polarized in its radial direction by, for example, the application of a voltage of the order of 3 kV/mm between the first and second electrodes 33 and 34. Therefore, when an alternating voltage is applied between the first and second electrodes 33 and 34, the piezoelectric vibrator 31 vibrates in its diametrical direction of the piezoelectric body 32 (hereinafter referred to as "cylindrical breathing vibration"). The cylindrical breathing vibration depends on at least one of d31 mode and d33 mode, and specifically, it is vibration that exhibits behavior illustrated in FIG. 5. That is, as illustrated in FIGS. 5(a) to 5(c), when a voltage is applied, piezoelectric effects cause the cylindrical piezoelectric body 32 to repeat increasing and reducing its diameter. With this, the vibrating membrane 40 vibrates in the vertical direction z.

The vibration of the piezoelectric body 32 may be self-excited vibration or separately excited vibration. In the case of separately excited vibration, because attachment of liquid to the surface of the piezoelectric vibrator 31 varies the resonant frequency, a control circuit to avoid the frequency from being varied is necessary. Accordingly, the vibration of the piezoelectric body 32 may preferably be self-excited vibration.

The wave of a voltage applied to the piezoelectric body 32 may be a sine wave, sawtooth wave, square wave, or other waves, for example. Among them, the wave of the voltage applied to the piezoelectric body 32 may preferably be a square wave. This is because the application of a square wave to the piezoelectric body 32 enables higher atomization efficiency.

Control for enabling or disabling atomization is made by control for turning on or off the application of a voltage to the piezoelectric body 32. Alternatively, it may be made by amplitude modulation or frequency modulation performed on the wave of a voltage applied to the piezoelectric body 32.

The first and second electrodes 33 and 34 are not particularly limited as long as a voltage can be applied to the piezoelectric body 32 therefrom. The first and second electrodes 33 and 34 can be made of a metal, such as silver, copper, gold, platinum, nickel, or tin, or an alloy, such as an alloy of chromium and nickel or an alloy of nickel and copper.

When the first and second electrodes 33 and 34 have low resistance to water, a protective film may be formed on the surface of each of the first and second electrodes 33 and 34. In particular, a protective film may preferably be disposed on the surface of at least the first electrode 33. This is because such a protective film can prevent deterioration of the first electrode 33 resulting from cavitation erosion occurring when vapor is attached to the surface of the first electrode 33.

The protective film is not particularly limited as long as it has resistance to water higher than that of each of the first and second electrodes 33 and 34. The protective film can be made of elastic resin, such as silicone resin, polyurethane resin, or polyester resin.

Examples of a method of forming the first and second electrodes 33 and 34 can include a thin-film forming method, such as Sputtering method, vapor deposition, or plating, and a method using conductive paste.

As illustrated in FIGS. 1 and 2, the vibrating membrane 40 is mounted on an opening 32a at a first side in an axial direction A of the piezoelectric body 32 so as to cover the opening 32a. Specifically, in the first embodiment, the vibrating membrane 40 is mounted on an end face 32b at the first side in the axial direction A of the piezoelectric body 32. The vibrating membrane 40 does not have to be disposed outside the piezoelectric body 32. The vibrating membrane 40 may be disposed inside the piezoelectric body 32, that is, in a hollow portion of the cylindrical piezoelectric body 32. The thickness of the vibrating membrane 40 is not particularly limited. For example, it can be on the order of 0.5 mm, for example.

The vibrating membrane 40 is a membrane vibrating in the vertical direction z by vibration of the piezoelectric body 32. The vibrating membrane 40 is not particularly limited as long as it is a membrane that can vibrate in the vertical direction z. The vibrating membrane 40 may preferably be a membrane that can vibrate mainly in 1st mode (fundamental mode) with vibration of the piezoelectric vibrator 31. In this case, the amount of the displacement of the vibrating membrane 40 can be large. Consequently, the vibrating membrane 40 can have a large region where atomization can be performed. Accordingly, a large number of through holes 43, which are described below, can be provided over a wide region, and atomization performance can be enhanced and the amount of possible atomization can be increased.

The material of the vibrating membrane 40 is not particularly limited. For example, the vibrating membrane 40 can be made of a material such as resin, ceramic, or metal. Among them, the vibrating membrane 40 may preferably be made of ceramic. With this, the vibrating membrane 40 can have an increased thickness, and it is easy to set the 1st mode as the dominant vibration mode of the vibrating membrane 40. When the vibrating membrane 40 is made of a metal material such as 42 alloy, phosphor bronze, or nickel silver, it may be preferable because the vibrating membrane 40 can be easily processed. In this case, because the vibrating membrane 40 is conductive, the vibrating membrane 40 can be part of means for electrically connecting with the piezoelectric body by providing electrical insulation with a part of the vibrating membrane 40.

Specifically, in the first embodiment, the vibrating membrane 40 includes a membrane main body 41 mounted on an end of the piezoelectric vibrator 31 and a through-hole formed member 42, which is an element different from the membrane main body 41. The membrane main body 41 has an opening 41a in its central portion. The through-hole formed member 42 is mounted at the opening 41a.

The material of the through-hole formed member 42 is not particularly limited. For example, the through-hole formed member 42 can be made of the same material as that of the membrane main body 41.

The shape of the through-hole formed member 42 is not particularly limited. For example, the through-hole formed member 42 can have dimensions of the order of 4.9 mm in diameter and 0.05 mm in thickness.

In the first embodiment, the opening 41a formed in the membrane main body 41 is smaller the diameter of the through-hole formed member 42, and the through-hole formed member 42 is pressed into the opening 41a, thus fixing the through-hole formed member 42 to the membrane main body 41. The method of fixing the through-hole formed member 42 to the membrane main body 41 is not particularly limited. For example, when the through-hole formed member 42 is made of a resin film with low stiffness or the like, the through-hole formed member 42 may be bonded to the membrane main body 41 using adhesive or the like. When the through-hole formed member 42 is made of metal, it may be fixed by being bonded to the membrane main body 41 that is made of ceramic, or it may be fixed by welding, brazing, or soldering, after the membrane main body 41 that is made of ceramic is subjected to plating.

Figure 4:
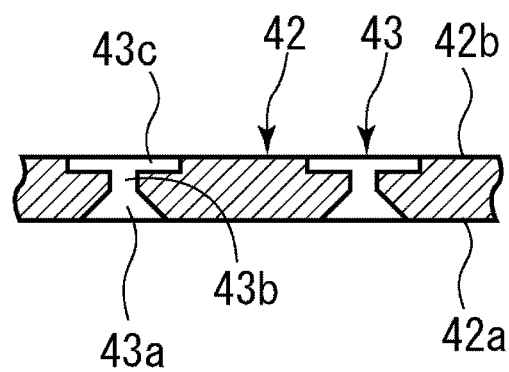
FIG. 4 is a schematic cross-sectional view of an enlarged part of a vibrating membrane.

The through-hole formed member 42 has the plurality of through holes (nozzle orifices) 43 passing through the through-hole formed member 42 in its thickness direction. The through holes 43 are used to generate vapor from the liquid 12. As illustrated in FIG. 4, each of the through holes 43 includes a spot facing hole 43a, a connection portion 43b, and a wide portion 43c. The spot facing hole 43a is opened in a lower surface 42a of the through-hole formed member 42.

Figure 6:
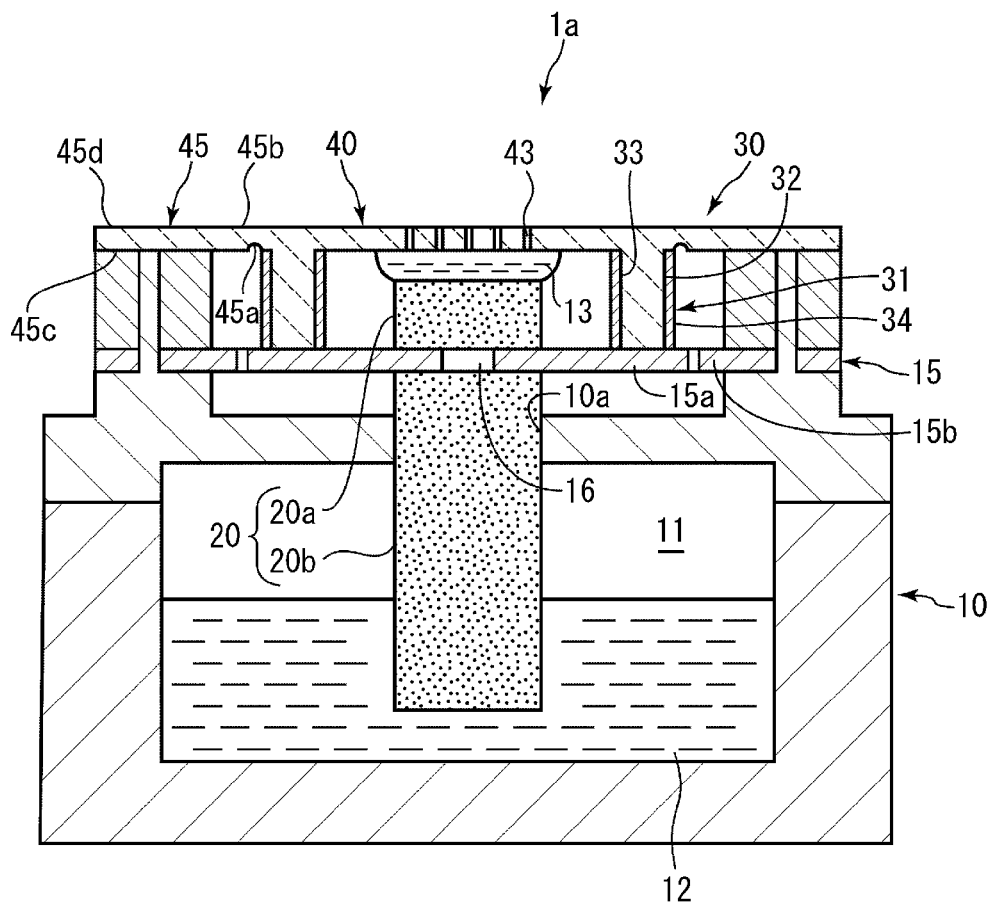
FIG. 6 is a schematic cross-sectional view of an atomizer of a second embodiment.
Figure 7:
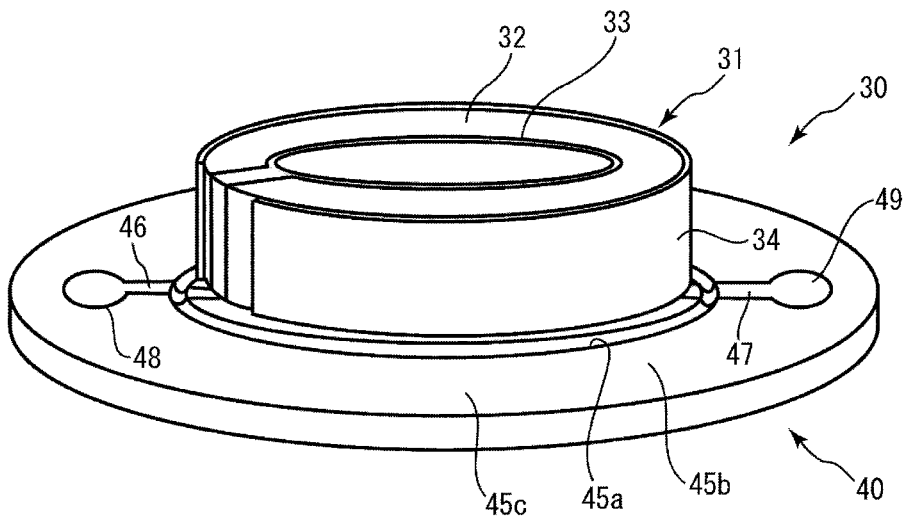
FIG. 7 is a schematic perspective view of an atomizing member in the second embodiment.

The spot facing hole 43a tapers from the lower surface 42a toward an upper surface 42b. The bottom end of the spot facing hole 43a is connected to the connection portion 43b. The connection portion 43b is substantially columnar and has substantially the same diameter as that of the bottom end of the spot facing hole 43a. The diameter of the connection portion 43b can be set to any value in response to the viscosity of the liquid 12 to be atomized. For example, the diameter of the connection portion 43b can be on the order of 5 to 20 μm. The bottom end of the connection portion 43b is connected to the wide portion 43c. The wide portion 43c has a columnar shape whose diameter is larger than that of the connection portion 43b. In FIG. 2 and FIG. 6, which is described below, for the sake of convenience of illustration, the through holes 43 are simply depicted as being columnar.

As described above, in the first embodiment, an example in which each of the through holes 43 includes the spot facing hole 43a, the connection portion 43b, and the wide portion 43c is described. However, the shape of the through hole 43 is not particularly limited to the one described above. For example, the through hole 43 may be taper or columnar.

The membrane main body 41 and the through-hole formed member 42 may be made of the same material or different materials. In particular, the through-hole formed member 42 may preferably be made of metal. This is because the formation of the through hole 43 in the case of the metallic through-hole formed member 42 is easier than, for example, that in the case of the ceramic through-hole formed member 42.

The method of forming the through hole 43 can be selected in response to the dimensions of the through hole 43, the material of the through-hole formed member 42, or the like. When the through-hole formed member 42 is made of metal, the through hole 43 can be formed by electroforming or laser processing, for example. When the through-hole formed member 42 is made of resin, the through hole 43 can be formed by a method using a laser, such as green-YAG laser, UV-YAG laser, or excimer laser, a method using chemical etching, a method using presswork, or other methods.

As illustrated in FIGS. 1 and 2, the atomizing member 30 is supported by the elastic film 15. The elastic film 15 is mounted to the atomizer main body 10 by a ring retainer 35.

The material of the elastic film 15 is not particularly limited. For example, the elastic film 15 can be made of resin, such as polyimide resin or polyethylene terephthalate (PET) resin. Alternatively, the elastic film 15 can be made of a metal leaf spring, for example.

The natural frequency of the elastic film 15 can be at or below 1 kHz, for example, and is typically lower than the frequency with which the piezoelectric body 32 can be driven (the natural frequency of the piezoelectric body 32 (e.g., approximately 100 kHz) and its neighborhood). Accordingly, even when the atomizing member 30 is supported by the elastic film 15, the vibration of the atomizing member 30 is not substantially conveyed to the elastic film 15. Accordingly, leakage of vibration energy to the elastic film 15 can be reduced, and degradation in energy efficiency caused by supporting the atomizing member 30 can be reduced.

Figure 3:
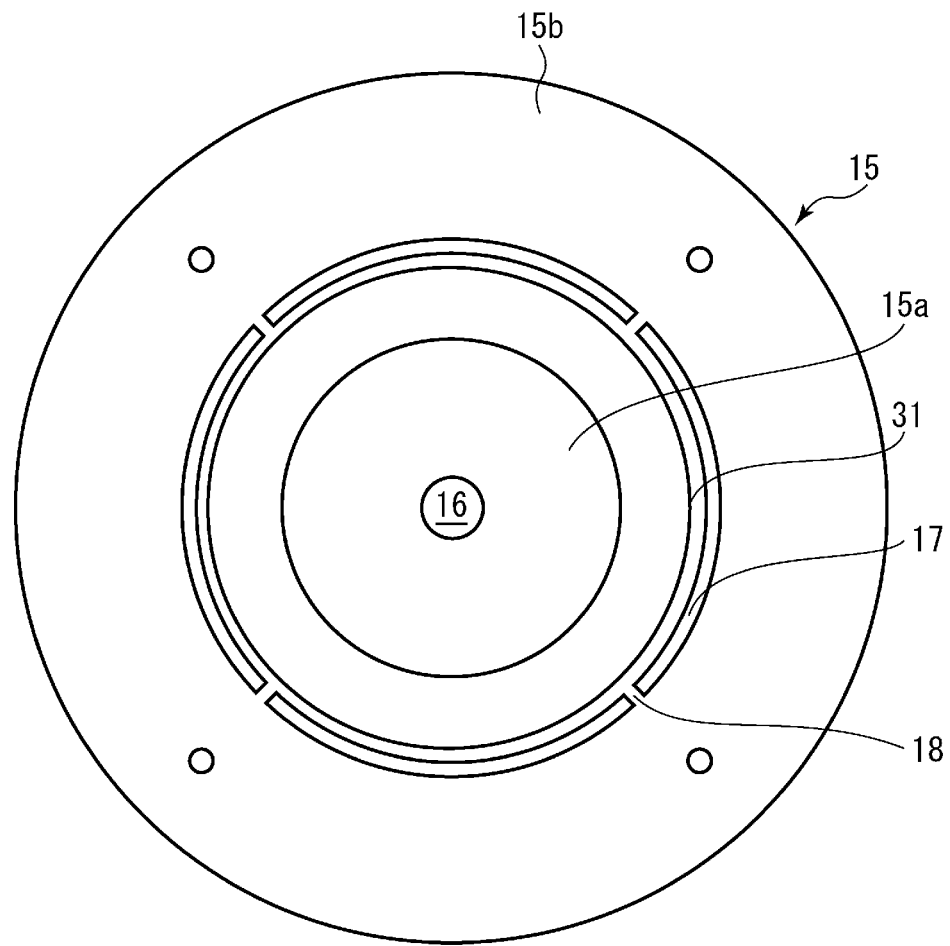
FIG. 3 is a schematic plan view of an elastic plate and a piezoelectric vibrator.

As illustrated in FIGS. 1 and 3, the elastic film 15 is disc-shaped. As illustrated in FIG. 2, the elastic film 15 has an opening 16 connecting a first liquid feeder 20a and a second liquid feeder 20b. As illustrated in FIGS. 1 and 3, the elastic film 15 has a plurality of arc-shaped openings 17 outside the opening 16. The openings 17 extend along the inner circumferential surface of the opening 16 and are spaced away from each other along the circumferential direction. The plurality of openings 17 partitions the elastic film 15 into an inner section 15a inside the openings 17 and an outer section 15b outside the openings 17. The inner section 15a is connected to the outer section 15b by a plurality of bridges 18 formed between the neighboring openings 17.

As illustrated in FIGS. 1 and 2, the atomizer 1 includes the liquid feeder 20. The liquid feeder 20 supplies the liquid 12 stored in the storage 11 toward the lower surface of the vibrating membrane 40.

Specifically, in the first embodiment, the liquid feeder 20 includes the first and second liquid feeders 20a and 20b. As illustrated in FIG. 2, the second liquid feeder 20b is supported by being inserted into an opening 10a of the atomizer main body 10. The lower end of the second liquid feeder 20b reaches the lower portion of the storage 11. The upper end of the second liquid feeder 20b reaches the lower end surface of the elastic film 15. The first liquid feeder 20a is disposed on the elastic film 15. The upper end of the first liquid feeder 20a is situated beneath the vibrating membrane 40. When the piezoelectric vibrator 31 is not driven, the upper end of the first liquid feeder 20a is not in contact with the vibrating membrane 40 and a gap 13 is present between the upper end of the first liquid feeder 20a and the vibrating membrane 40. The distance of the gap 13 can be set in response to the viscosity of the liquid or the like so as to be filled with liquid. The distance of the gap 13 can be set to approximately 0.05 to 1 mm, for example.

The first and second liquid feeders 20a and 20b have the function of soaking the liquid 12 up by a capillary action. Therefore, the liquid 12 stored in the storage 11 is soaked up by the second liquid feeder 20b and supplied to the first liquid feeder 20a. The liquid 12 supplied to the first liquid feeder 20a is soaked up to the gap 13 by the first liquid feeder 20a. Then, because the vibrating membrane 40 is positioned above the gap 13, the liquid 12 soaked up by the first liquid feeder 20a is accumulated in the gap 13. This enables the liquid 12 to be supplied to the vibrating membrane 40.

In the first embodiment, the first and second liquid feeders 20a and 20b are not particularly limited as long as they allow a capillary action. The first and second liquid feeders 20a and 20b can be made of felt, a nonwoven fabric, nonwoven paper, or porous resin, for example.

Figure 12:
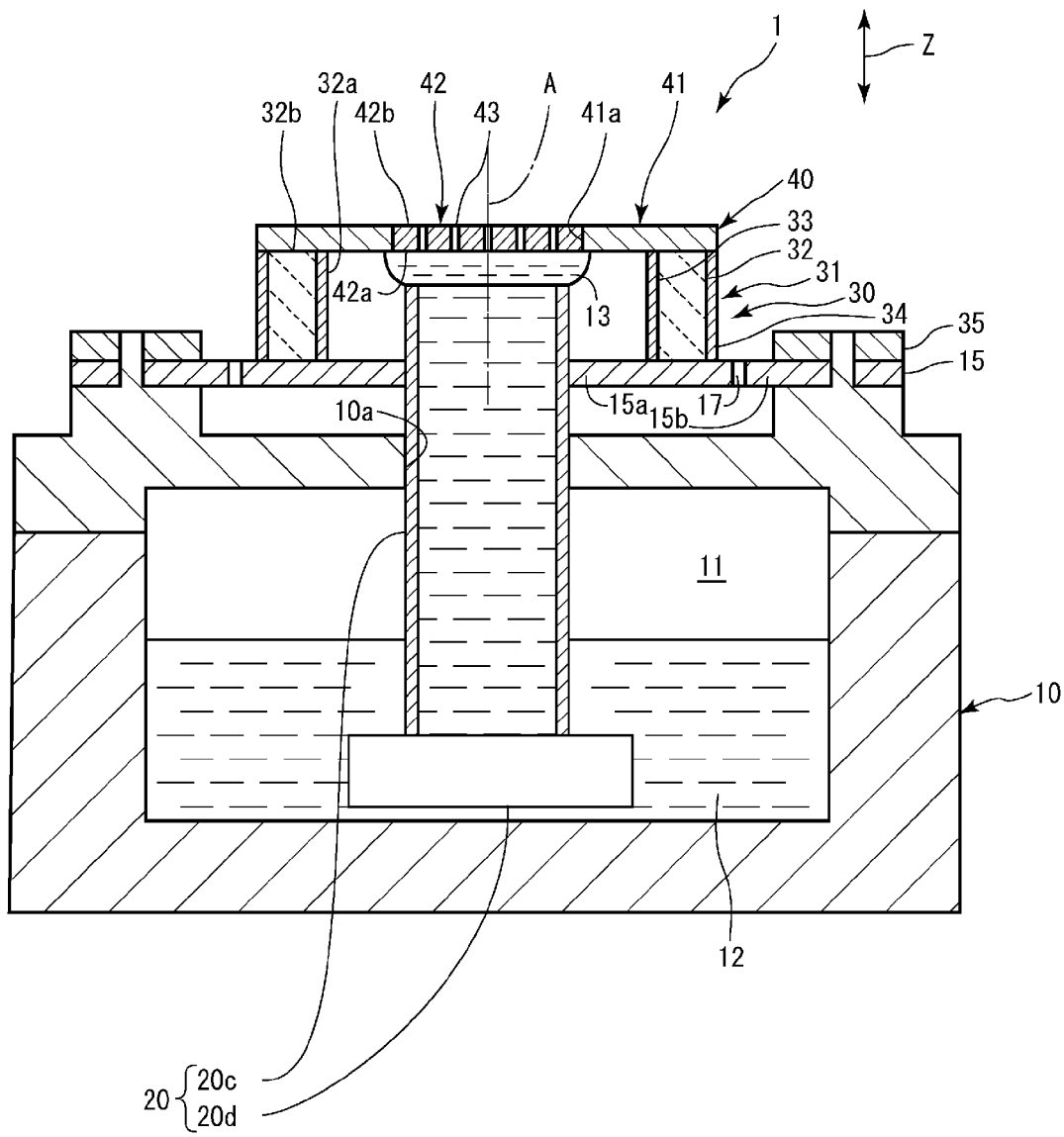
FIG. 12 is a schematic cross-sectional view of an atomizer of a second modification example.
Figure 13:
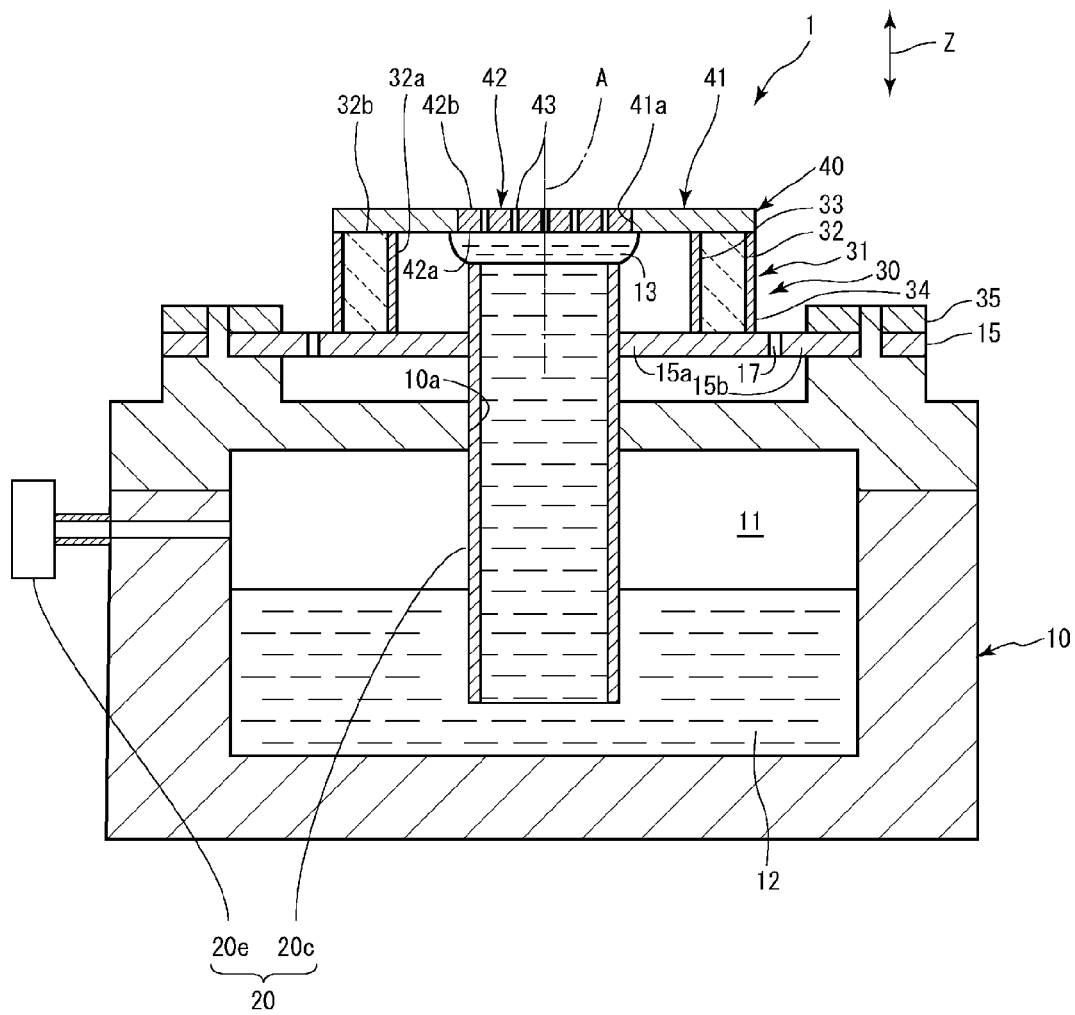
FIG. 13 is a schematic cross-sectional view of an atomizer of a third modification example.

However, in the present invention, the liquid feeder to the vibrating membrane is not limited to one that allows a capillary action. The liquid feeder 20 may include liquid supply means, such as a pump 20d or a blower 20e, and a tube 20c for supplying liquid from the liquid supply means to the vibrating membrane 40, as illustrated in FIGS. 12 and 13, for example. In this case, the distance between the end of the tube 20c and the vibrating membrane 40 may preferably be one that does not cause the end of the tube 20c and the vibrating membrane 40 to interfere with each other when the vibrating membrane 40 vibrates, and it may more preferably be equal to or less than the distance between the end of the tube 20c and the highest rise point of liquid raised by surface tension.

For the atomizer 1 of the first embodiment, when a voltage is applied between the first and second electrodes 33 and 34, the piezoelectric vibrator 31 performs cylindrical breathing vibration, as illustrated in FIGS. 5(a) to 5(c). In response to this cylindrical breathing vibration of the piezoelectric vibrator 31, the vibrating membrane 40 vibrates and repeats displacement in the vertical direction z. This cause the liquid 12 supplied to the gap 13 by the liquid feeder 20 to be sprayed through the through holes 43.

The mode of the cylindrical breathing vibration illustrated in FIGS. 5(a) to 5(c) is an example. The mode of the cylindrical breathing vibration may vary depending on the frequency of the cylindrical breathing vibration. Specifically, the mode illustrated in FIGS. 5(a) to 5(c) is an example in which, when a section of the piezoelectric vibrator 31 opposite to the vibrating membrane 40 reduces its diameter, the vibrating membrane 40 is displaced in a concave shape. However, depending on the frequency, when the section of the piezoelectric vibrator 31 opposite to the vibrating membrane 40 reduces its diameter, the vibrating membrane 40 may be displaced in a convex shape. That is, depending on the frequency of the cylindrical breathing vibration, the phase of the vibration of the vibrating membrane 40 may be shifted by 180°.

In this way, in the first embodiment, the cylindrical breathing vibration of the cylindrical piezoelectric body 32 excites a membrane vibration of the vibrating membrane 40. Therefore, the membrane vibration of the vibrating membrane 40 can be excited with higher efficiency, in comparison with, for example, when the membrane vibration of the vibrating membrane is excited by transverse effects of the disc-shaped piezoelectric body. Accordingly, high atomization efficiency can be achieved. As a result, power consumption of the atomizer 1 can be reduced.

In addition, vibration energy of the vibrating membrane 40 can be increased with the same power consumption. Therefore, the maximum number of through holes which atomization can be performed is large. Accordingly, the number of through holes 43 can be increased. As a result, a larger quantity of atomization is obtainable with the same power consumption.

The use of the cylindrical breathing vibration enables large vibration amplitude, and thus sprayed vapor can be flown farther.

In the case of cylindrical breathing vibration of the cylindrical piezoelectric body 32, the outer circumferential portion at the end of the piezoelectric body 32 along its axial direction is a node. That is, the displacement of the outer circumferential portion at the end of the piezoelectric body 32 in its axial direction when the piezoelectric body 32 is vibrating is small. Accordingly, supporting the piezoelectric vibrator 31 is easy. Supporting the end of the piezoelectric vibrator 31 in the axial direction, as in the first embodiment, prevents the elastic film 15 being a support from interfering with the vibration of the piezoelectric vibrator 31. The vibration of the piezoelectric vibrator 31 is not easily conveyed to the elastic film 15. Accordingly, vibration damping can be reduced and a decrease in vibration efficiency of the piezoelectric vibrator 31 caused by the support can be suppressed. As a result, higher atomization efficiency and lower power consumption can be achieved.

Figure 8:
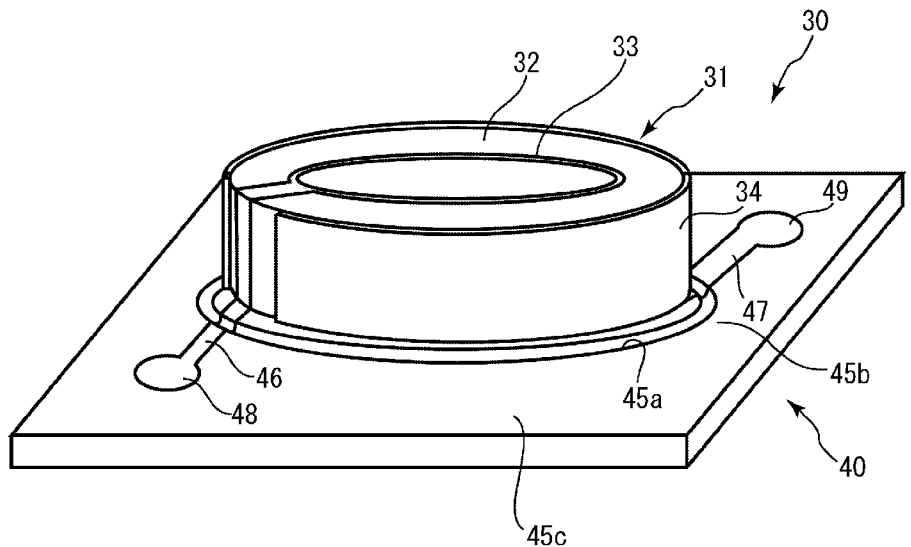
FIG. 8 is a schematic perspective view of an atomizing member in a modification example.
Figure 9:
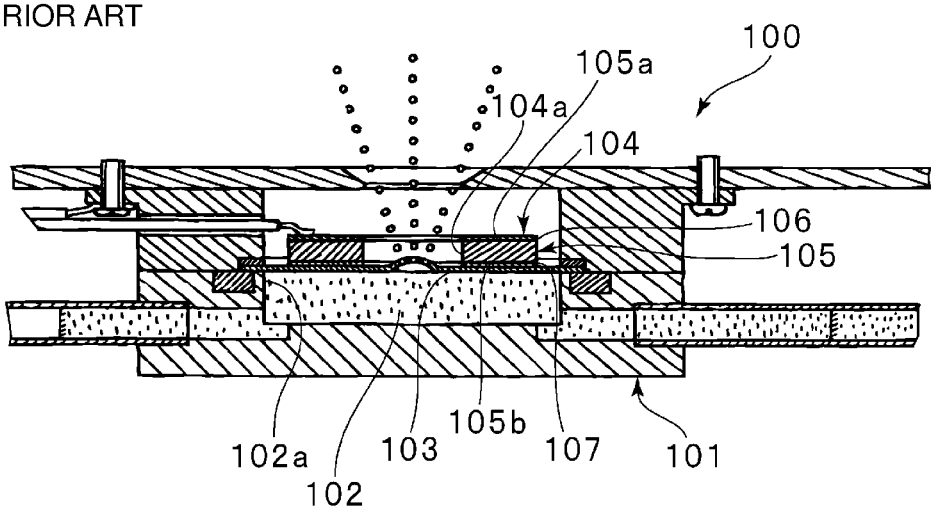
FIG. 9 is a cross-sectional view of an atomizer described in Patent Literature 1.
Figure 10:
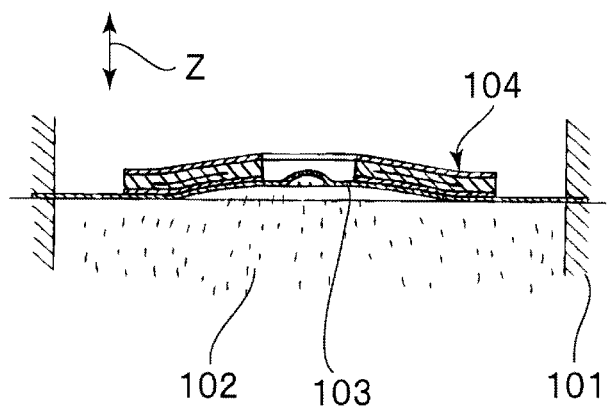
FIG. 10 is a cross-sectional view for describing operation of a piezoelectric vibrator and a nozzle plate of the atomizer described in Patent Literature 1. Specifically.
Figure 11:
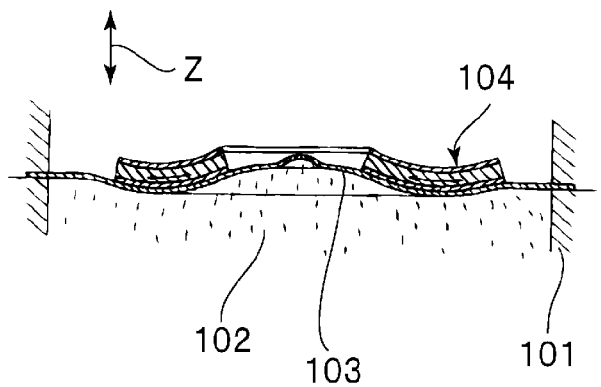
FIG. 11 is a cross-sectional view for describing operation of the piezoelectric vibrator and the nozzle plate of the atomizer described in Patent Literature 1. Specifically.

Specifically, for example, for an atomizer that uses a piezoelectric body vibrated by transverse effects, as described in Patent Literature 1, the atomization voltage is on the order of 20 Vpp. In contrast, for the atomizer 1 using the piezoelectric body 32 performing cylindrical breathing vibration of the first embodiment, the atomization voltage can be reduced to approximately 10 Vpp, for example. The power consumption of a traditional atomizer that uses a piezoelectric body vibrated by transverse effects is on the order of several hundred of mW, whereas that of the atomizer 1 using the piezoelectric body 32 performing cylindrical breathing vibration can be reduced to below several tens of mW. This result also reveals that the use of an elastic body performing cylindrical breathing vibration enables high atomization efficiency and low power consumption.

In the first embodiment, the central section where the through holes 43 of the vibrating membrane 40 are disposed is composed of the through-hole formed member 42, which is a different element. Therefore, the vibrating membrane 40 can be easily produced. In addition, the through-hole formed member 42 can be made of a material different from that of the membrane main body 41. Accordingly, the degree of freedom in design of the membrane main body 41 and the through-hole formed member 42 is improved, and the membrane main body 41 and the through-hole formed member 42 can more precisely conform to specifications required for them. That is, the membrane main body 41 can be more suited for vibration, and the through-hole formed member 42 can be more suited for atomization.

In the first embodiment, the liquid feeder 20 supplies the liquid 12 to a surface of the vibrating membrane 40 on which the piezoelectric vibrator 31 is disposed. In other words, the liquid feeder 20 is positioned adjacent to a side opposite to a side from which vapor diverges of the vibrating membrane 40. Accordingly, the angle of divergence of spraying vapor can be large, and thus spraying vapor on a wider region can be achieved.

Other embodiments and modification examples are described below. In the description of the other embodiments and modification examples below, a member having substantially the same function as that in the above first embodiment is referred to by the same reference numeral, and the detailed description is omitted.

Second Embodiment

FIG. 6 is a schematic cross-sectional view of an atomizer of the second embodiment. FIG. 7 is a perspective view of an atomizing member of the second embodiment.

An atomizer 1*a* of the second embodiment has substantially the same configuration as that of the atomizer 1 of the above first embodiment, except for the form of the atomizing member 30 and the supporting manner of the atomizing member 30. In the second embodiment, sections in the atomizing member 30 other than the first and second electrodes 33 and 34 are integrally formed from ceramic. Specifically, in the second embodiment, the vibrating membrane 40, the piezoelectric body 32, and a flange 45, which is described below, are integrally formed from piezoelectric ceramic. Therefore, it is not necessary to bond the members, so the atomizing member 30 can be easily produced. The integral formation of the vibrating membrane 40, the piezoelectric body 32, and the flange 45 can improve the vibration efficiency. Accordingly, higher atomization efficiency and lower power consumption can be achieved. However, the vibrating membrane 40, the piezoelectric body 32, and the flange 45 can be formed as different elements.

As illustrated in FIGS. 6 and 7, in the second embodiment, the piezoelectric vibrator 31 includes the ring flange 45. The flange 45 is connected to the upper end section of the piezoelectric body 32 and outwardly extends from the piezoelectric body 32 in a direction substantially parallel with the upper end surface of the piezoelectric body 32. The piezoelectric vibrator 31 is mounted on the atomizer main body 10 at the flange 45. In this way, the flange 45 facilitates mounting of the piezoelectric vibrator 31 on the atomizer main body 10.

The flange 45 is connected to the outer circumferential portion of the piezoelectric body 32 in the axial direction A, the end having small displacement in vibration. Therefore, even when the flange 45 is fixed, inhibition on the vibration of the piezoelectric body 32 is small. Consequently, degradation in vibration efficiency in response to fixation of the piezoelectric vibrator 31 can be reduced.

In the second embodiment, the flange 45 is toroidal. Accordingly, inhibition on the vibration of the piezoelectric body 32 is smaller.

In addition, in the second embodiment, a connection portion 45*b* of the flange 45 which is connected to the piezoelectric body 32 has an annular groove 45*a*. Therefore, a section of the connection portion 45*b* where the groove 45*a* is formed is thinner than the other sections of the flange 45. Accordingly, inhibition on the vibration of the piezoelectric body 32 is smaller, and degradation in vibration efficiency is more efficiently reduced. The groove 45*a* enables reflection of the vibration of the piezoelectric body 32, and the vibration can be efficiently confined in the piezoelectric body 32. Accordingly, the efficiency of conveying the vibration of the piezoelectric body 32 to the vibrating membrane 40 can be more improved.

In the second embodiment, the groove 45*a* is ring-shaped entirely around the piezoelectric body 32. Alternatively, however, the groove 45*a* may be disposed in part around the piezoelectric body 32. In the second embodiment, the groove 45*a* is disposed in a lower surface 45*c* of the flange 45. Alternatively, however, the groove may be disposed in an upper surface 45*d* of the flange 45, or may be disposed in both the upper surface 45*d* and the lower surface 45*c*. Additionally, a plurality of grooves may be disposed on different sites in the diametrical direction of the piezoelectric body 32. In place of the groove, an aperture may be disposed in the flange 45.

If the groove 45*a* is too deep, the durability of the flange 45 tends to be low. Therefore, the minimum value of the thickness of the flange 45 in the section where the groove 45*a* is disposed may preferably be on the order of 0.2 times to 0.5 times the thickness of the flange 45 in the section where the groove 45*a* is not disposed.

The flange 45 can reduce attachment of generated vapor to the surfaces of the first and second electrodes 33 and 34. Accordingly, even if the piezoelectric vibrator 31 vibrates at a high frequency, degradation of the first and second electrodes 33 and 34 resulting from cavitation erosion can be efficiently reduced.

As illustrated in FIG. 7, the first and second electrodes 33 and 34 are connected to first and second electrode pads 48 and 49 by first and second wires 46 and 47, respectively. The first and second electrode pads 48 and 49 are disposed on the lower surface 45*c* of the flange 45. Therefore, in the second embodiment, degradation of the first and second electrode pads 48 and 49 resulting from cavitation erosion can also be efficiently reduced.

The second electrode 34 is disposed in a section other than a part of the outer circumferential surface of the piezoelectric body 32 in its circumferential direction. The first wire 46 connecting the first electrode 33 and the first electrode pad 48 is disposed in a section of the outer circumferential surface of the piezoelectric body 32 where the second electrode 34 is not disposed.

Modification Examples

In the above second embodiment, an example in which the flange 45 is toroidal is described. However, the shape of the flange in the present invention is not particularly limited. For example, as illustrated in FIG. 8, the flange 45 may be substantially rectangular.

In the above second embodiment, an example in which the annular groove 45a in the connection portion 45b of the flange 45 connected to the piezoelectric body 32 prevents vibration of the piezoelectric body 32 from being conveyed to the flange 45 is described. However, the method of reducing conveyance of the vibration of the piezoelectric body 32 to the flange 45 is not limited to the method using the annular groove 45a. Making vibration propagation characteristics of the connection portion 45b different from those of the sections of the flange 45 other than the connection portion 45b can reduce conveyance of the vibration of the piezoelectric body 32 to the flange 45. Examples of the method of making vibration propagation characteristics of the connection portion 45b different from those of the sections of the flange 45 other than the connection portion 45b include forming the groove in the connection portion 45b, as described above, forming a projection (projection that is annular or that is annular but is cut in part), mounting a different member on the connection portion 45b, and forming a hole (hole that is annular or that is annular but is cut in part).

Third Embodiment

Figure 14:
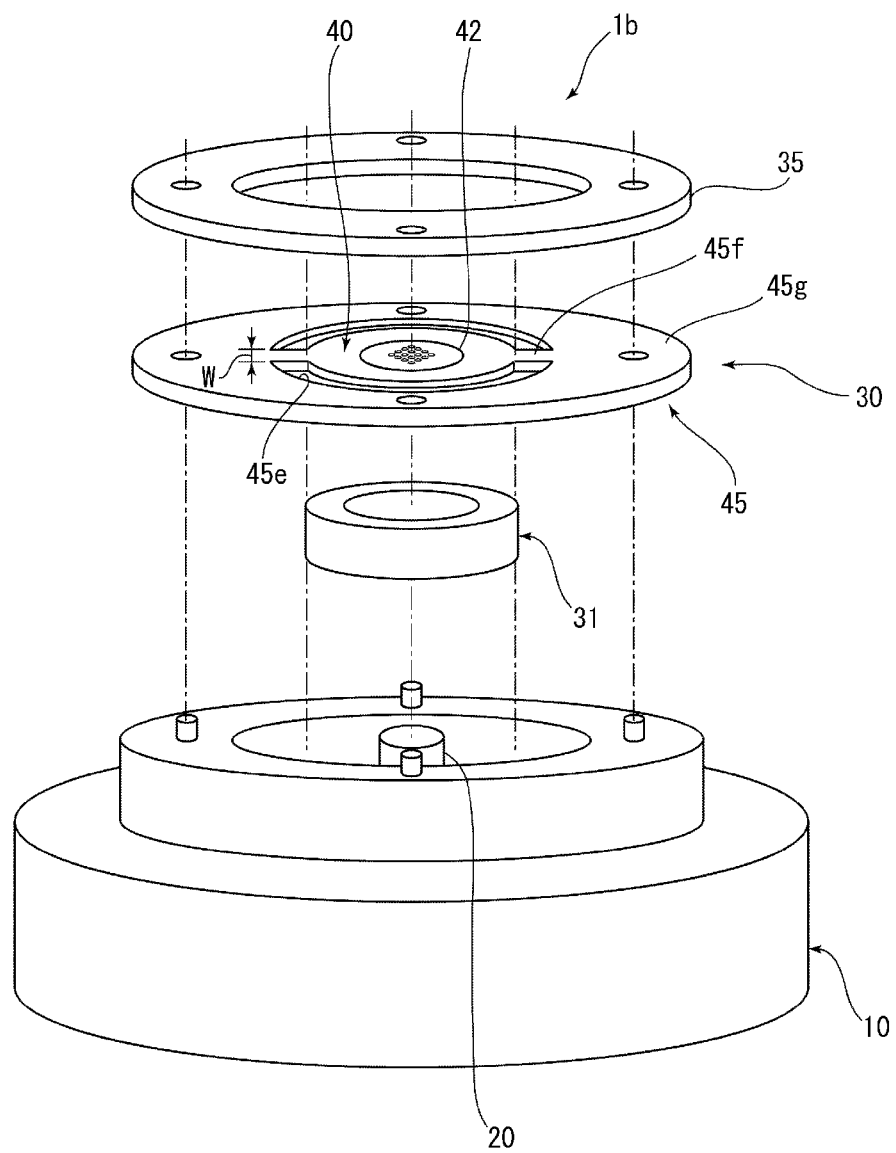
FIG. 14 is a schematic exploded perspective view of an atomizer of a third embodiment.
Figure 15:
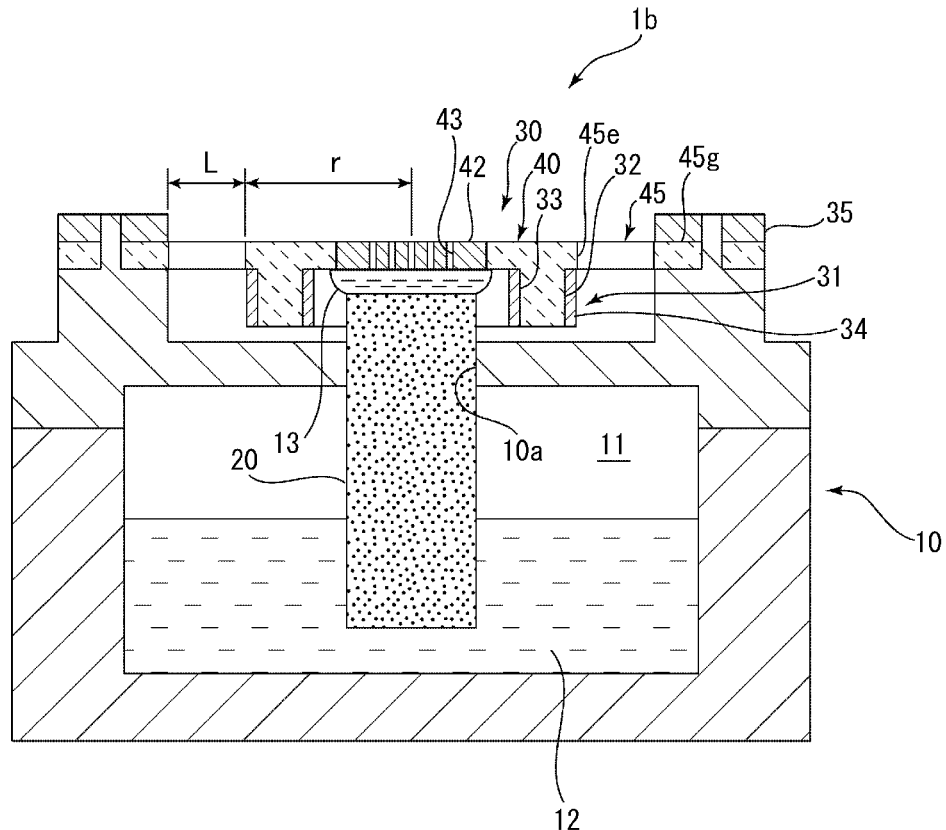
FIG. 15 is a schematic cross-sectional view of the atomizer of the third embodiment.

FIG. 14 is a schematic exploded perspective view of an atomizer of a third embodiment. FIG. 15 is a schematic cross-sectional view of the atomizer of the third embodiment.

An atomizer 1b of the third embodiment is different from the atomizer 1a of the second embodiment in that the elastic film 15 is not included, the liquid feeder 20 is formed integrally, and the atomizing member 30 has a different configuration. Here, the configuration of the atomizing member 30 in the third embodiment is described with reference to FIGS. 14 and 15.

For the third embodiment, the atomizing member 30 includes a plurality of through holes 45e extending along its circumferential direction and being arranged along the circumferential direction. The plurality of through holes 45e form at least two bridges 45f (see FIG. 14) connecting a peripheral portion 45g being the section of the flange 45 supported by the atomizer main body 10 and the vibrating membrane 40. The at least two bridges 45f are spaced at regular intervals along the circumferential direction. In the third embodiment, specifically, the two bridges 45f are provided. However, the number of bridges in the present invention is not particularly limited. For example, two to four bridges may be provided.

The width (W) of each of the bridges 45f illustrated in FIG. 14 is not particularly limited. For example, the width (W) of the bridge 45f can be on the order of 0.05 times to 0.7 times the length (L) of the bridge 45f along the radial direction illustrated in FIG. 15.

In the third embodiment, the length (L) of the bridge 45f along the radial direction is within the range of 30% to 50%, 70% to 90%, or 115% to 120% of the radius (r) of the vibrating membrane 40. Therefore, the occurrence of resonance of a frequency near the resonant frequency of the vibrating membrane 40 can be efficiently reduced. Accordingly, with the atomizer 1b of the third embodiment, the occurrence of unnecessary vibration can be reduced, and satisfactory atomization characteristics can be achieved.

This advantageous effect is described below in further details.

Figure 16:
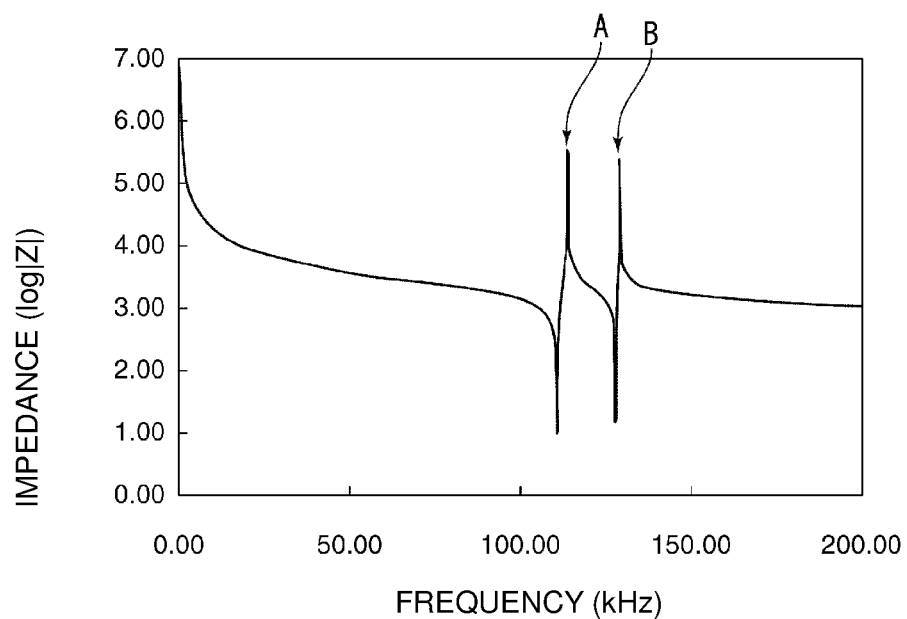
FIG. 16 is a graph that represents impedance characteristics of an atomizing member when the ratio (L/r) of the length (L) of a bridge along its radial direction to the radius (r) of a vibrating membrane is 80%.
Figure 17:
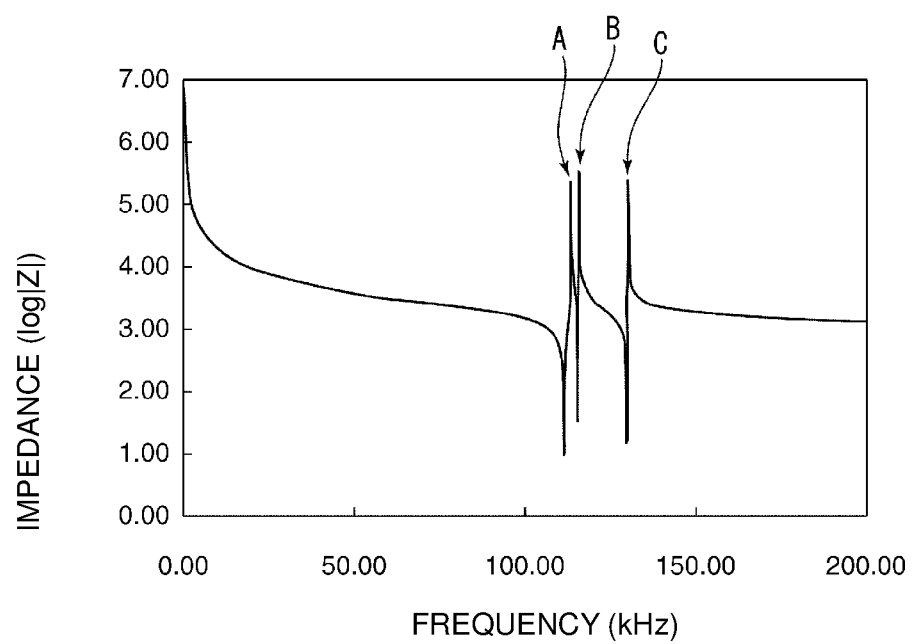
FIG. 17 is a graph that represents impedance characteristics of the atomizing member when the ratio (L/r) of the length (L) of the bridge along its radial direction to the radius (r) of the vibrating membrane is 100%.

FIG. 16 is a graph that represents impedance characteristics of the atomizing member when the ratio (L/r) of the length (L) of the bridge along its radial direction to the radius (r) of the vibrating membrane is 80%. FIG. 17 is a graph that represents impedance characteristics of the atomizing member when the ratio (L/r) of the length (L) of the bridge along its radial direction to the radius (r) of the vibrating membrane is 100%.

As illustrated in FIG. 16, when the ratio (L/r) is 80%, a spurious response resulting from unnecessary vibration is not observed between vibration in 1st mode indicated by A in FIG. 16 and vibration in 2nd mode indicated by B. In contrast, as illustrated in FIG. 17, when the ratio (L/r) is 100%, a spurious response resulting from unnecessary vibration indicated by C was observed between vibration in 1st mode indicated by A and vibration in 2nd mode indicated by B.

Then, when the width (W) of the bridge 45f is changed, a relationship between the ratio (L/r) of the length (L) of the bridge along its radial direction to the radius (r) of the vibrating membrane and the presence or absence of a spurious response was examined.

Figure 18:
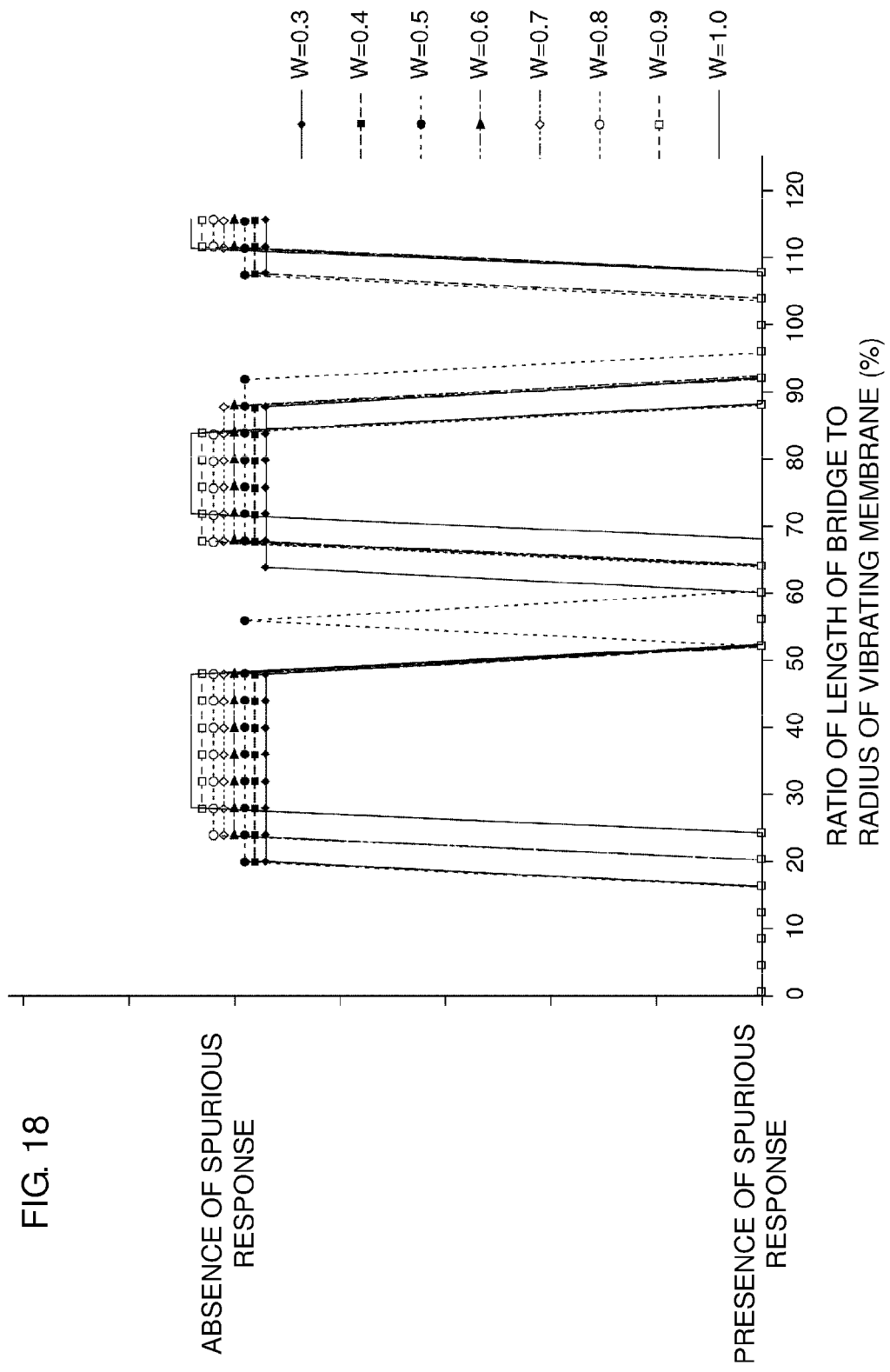
FIG. 18 is a graph that represents a relationship between the ratio (L/r) of the length (L) of the bridge along its radial direction to the radius (r) of the vibrating membrane and the presence or absence of a spurious response.

FIG. 18 is a graph that represents a relationship between the ratio (L/r) of the length (L) of the bridge along its radial direction to the radius (r) of the vibrating membrane and the presence or absence of a spurious response.

The results illustrated in FIG. 18 reveal that, irrespective of the width (W) of the bridge 45f, when the length (L) of the bridge 45f along the radial direction is within the range of 30% to 50%, 70% to 90%, or 115% to 120% of the radius (r) of the vibrating membrane 40, no spurious response resulting from unnecessary vibration occurs. The above results reveal that setting the length (L) of the bridge 45f along the radial direction to within the range of 30% to 50%, 70% to 90%, or 115% to 120% of the radius (r) of the vibrating membrane 40 can reduce the occurrence of unnecessary vibration, and satisfactory atomization characteristics can be achieved.

Fourth Modification Example

Figure 19:
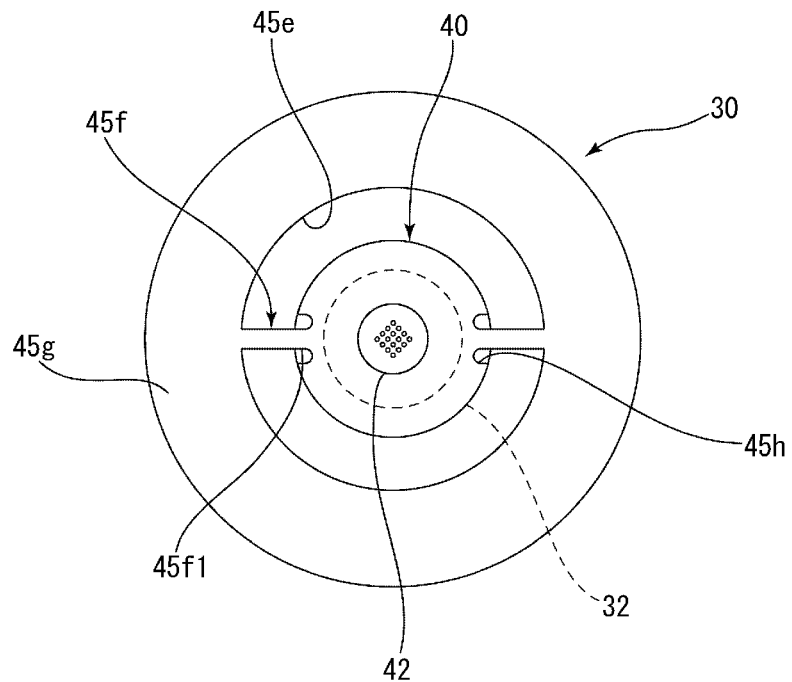
FIG. 19 is a schematic plan view of an atomizing member in a fourth modification example.
Figure 20:
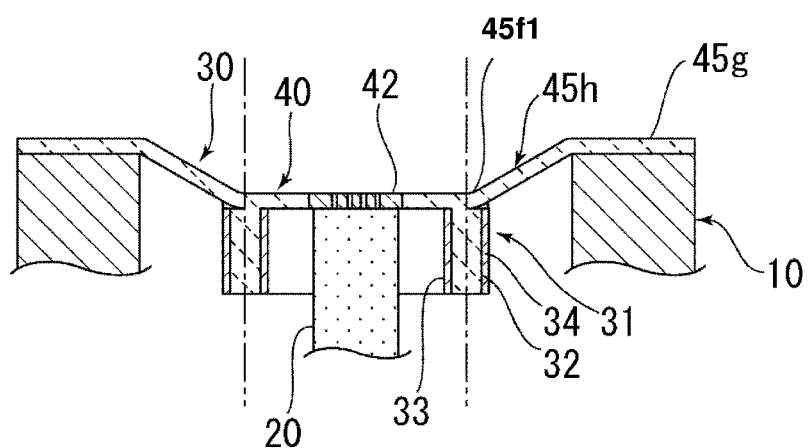
FIG. 20 is a schematic cross-sectional view of a part of an atomizer in the fourth modification example.

FIG. 19 is a schematic plan view of an atomizing member in a fourth modification example. FIG. 20 is a schematic cross-sectional view of a part of an atomizer in the fourth modification example.

The fourth modification example is a modification example of the above third embodiment. The atomizer of the fourth modification example differs from the atomizer 1b of the above third embodiment in the configuration of each of the vibrating membrane 40 and the bridge 45f.

As illustrated in FIG. 19, a cut portion 45h reaching the central portion of the piezoelectric body 32 in the thickness direction is disposed at each of both sides of a section of the vibrating membrane 40 in the circumferential direction that is connected to the bridge 45f. A section 45f1 of the bridge 45f positioned between the cut portions 45h in the circumferential direction is not connected to the piezoelectric body 32. The central portion of the piezoelectric body 32 in the thickness direction is a node. Therefore, in the fourth modification example, the vibrating membrane 40 can be supported at the node. Accordingly, more satisfactory atomization characteristics are obtainable.

In the fourth modification example, as illustrated in FIG. 20, the piezoelectric body 32 is connected to the lower side of the vibrating membrane 40 in the vertical direction. Therefore, the vibrating membrane 40 is positioned below the peripheral portion 45g by the weight of the piezoelectric body 32. Consequently, the section 45f1 of the bridge 45f positioned between the cut portions 45h in the circumferential direction and the piezoelectric body 32 are spaced away from each other. Consequently, contact between the portion 45f1 and the piezoelectric body 32 can be reduced. Accordingly, abrasion of the section 45f1 can be reduced. As a result, for the fourth modification example, the life of the atomizer can be increased.

The vibrating membrane 40 and the peripheral portion 45g may be flush with each other.

REFERENCE NUMBER LIST 1, 1a, 1b atomizer
10 atomizer main body
10a opening
11 storage
12 liquid
13 gap
15 elastic film
15a inner section
15b outer section
16 opening
17 opening
18 bridge
20 liquid feeder
20a first liquid feeder
20b second liquid feeder
20c tube
20d pump
20e blower
30 atomizing member
31 piezoelectric vibrator
32 piezoelectric body
32a opening
32b end face
33 first electrode
34 second electrode
40 vibrating membrane
41 membrane main body
41a opening
42 through-hole formed member
42a lower surface of through-hole formed member
42b upper surface of through-hole formed member
43 through hole
43a spot facing hole
43b connection portion
43c wide portion
45 flange
45a annular groove
45b connection portion
45c lower surface of flange
45d upper surface of flange
45e through hole
45f bridge
45f1 section of bridge 45f positioned between cut portions 45h in circumferential direction
45g peripheral portion
45h cut portion
46 first wire
47 second wire
48 first electrode pad
49 second electrode pad

The invention claimed is:

1. An atomizing member comprising:
a piezoelectric vibrator that includes a cylindrical piezoelectric body, a first electrode disposed on an inner circumferential surface of the piezoelectric body, and a second electrode disposed on an outer circumferential surface of the piezoelectric body and configured to perform cylindrical breathing vibration; and
a vibrating membrane disposed on an opening of the piezoelectric body at a first side in an axial direction thereof so as to cover the opening, the vibrating membrane having a through hole in a central portion thereof,
wherein the piezoelectric vibrator includes a flange connected to a section of the piezoelectric body at the first side in the axial direction thereof, the flange extending outwardly in a diametrical direction from the section at the first side.

2. The atomizing member according to claim 1, wherein the piezoelectric body and the vibrating membrane are integral with each other.

3. The atomizing member according to claim 1, wherein the flange is integral with the piezoelectric body.

4. The atomizing member according to claim 1, wherein the flange includes a connection portion that is connected to the piezoelectric body and has vibration propagation characteristics different from those of other sections of the flange.

5. The atomizing member according to 1, wherein the flange includes a connection portion that is connected to the piezoelectric body and has a groove.

6. The atomizing member according to claim 1, wherein the piezoelectric vibrator further includes a first electrode pad connected to the first electrode and a second electrode pad connected to the second electrode, and the first and second electrode pads are disposed on a surface of the flange at a second side in the axial direction of the piezoelectric body.

7. The atomizing member according to claim 1, wherein the central portion of the through hole of the vibrating membrane comprises a through-hole formed member that is a different element from other sections of the vibrating membrane.

8. The atomizing member according to claim 7, wherein the through-hole formed member is metal.

9. The atomizing member according to claim 7, wherein the through-hole formed member and the other sections of the vibrating membrane each comprise the same material.

10. An atomizer comprising:
the atomizing member according to claim 1;
an atomizer main body on which the piezoelectric vibrator is mounted, the atomizer main body including a storage for storing liquid; and
a liquid feeder that supplies the liquid stored in the storage to the section of the vibrating membrane where the through hole is disposed.

11. The atomizer according to claim 10, wherein the liquid feeder is configured to supply the liquid from a second side in the axial direction of the piezoelectric body to the vibrating membrane.

12. The atomizer according to claim 10, wherein the piezoelectric vibrator includes a flange connected to a section of the piezoelectric body at the first side in the axial direction thereof, the flange extending outwardly in a diametrical direction from the section at the first side, the flange including a peripheral portion in the diametrical direction supported by the atomizer main body,
the flange also including at least two bridges formed by a plurality of through holes extending in a circumferential direction thereof, the at least two bridges connecting the peripheral portion and the vibrating membrane, and
a length of each of the at least two bridges is within a range of 30% to 50%, 70% to 90%, or 115% to 120% of a radius of the vibrating membrane.

13. The atomizer according to claim 12, wherein a cut portion reaching a central portion in a thickness direction of the piezoelectric body is disposed at each of both sides of a first section of the vibrating membrane in the circumferential direction, the section being connected to each of the bridges, and a second section positioned between the cut portions in the circumferential direction of the bridge is not connected to the piezoelectric body.

14. The atomizer according to claim 13, wherein the piezoelectric body is arranged below the vibrating membrane in a vertical direction thereof.

15. An atomizer comprising:
an atomizing member including:
  a piezoelectric vibrator that includes a cylindrical piezoelectric body, a first electrode disposed on an inner circumferential surface of the piezoelectric body, and a second electrode disposed on an outer circumferential surface of the piezoelectric body and configured to perform cylindrical breathing vibration, and
  a vibrating membrane disposed on an opening of the piezoelectric body at a first side in an axial direction thereof so as to cover the opening, the vibrating membrane having a through hole in a central portion thereof;
an atomizer main body on which the piezoelectric vibrator is mounted, the atomizer main body including a storage for storing liquid; and
a liquid feeder that supplies the liquid stored in the storage to the section of the vibrating membrane where the through hole is disposed, wherein the piezoelectric vibrator includes a flange connected to a section of the piezoelectric body at the first side in the axial direction thereof, the flange extending outwardly in a diametrical direction from the section at the first side, the flange including a peripheral portion in the diametrical direction supported by the atomizer main body, wherein the flange also including at least two bridges formed by a plurality of through holes extending in a circumferential direction thereof, the at least two bridges connecting the peripheral portion and the vibrating membrane, and wherein a length of each of the at least two bridges is within a range of 30% to 50%, 70% to 90%, or 115% to 120% of a radius of the vibrating membrane.

16. The atomizer according to claim 15, wherein a cut portion reaching a central portion in a thickness direction of the piezoelectric body is disposed at each of both sides of a first section of the vibrating membrane in the circumferential direction, the section being connected to each of the bridges, and a second section positioned between the cut portions in the circumferential direction of the bridge is not connected to the piezoelectric body.

17. The atomizer according to claim 16, wherein the piezoelectric body is arranged below the vibrating membrane in a vertical direction thereof.

* * * * *